Figure 1A:
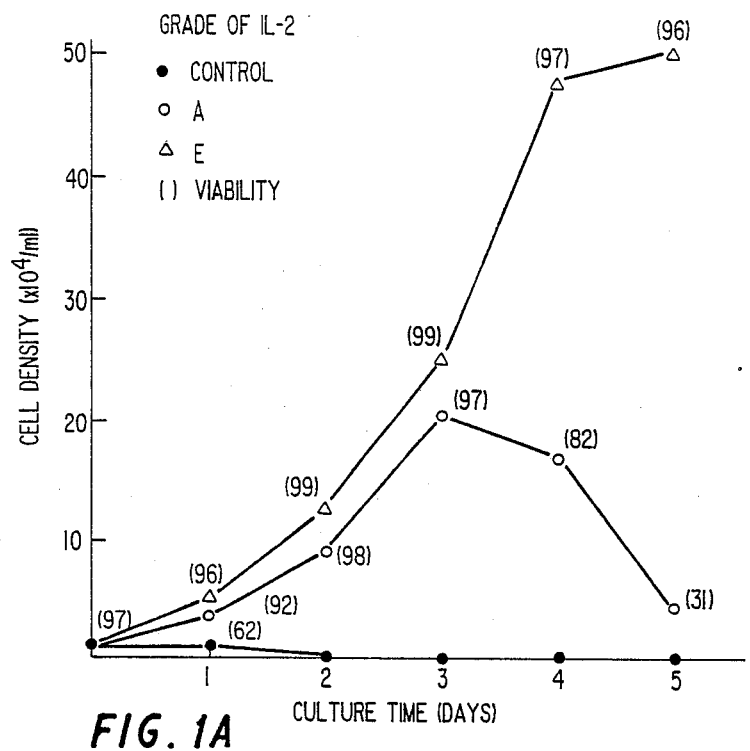

United States Patent [19]
Yoshimoto et al.

[11] Patent Number: 4,789,658
[45] Date of Patent: Dec. 6, 1988

[54] IMMUNOPROPHYLACTIC AND IMMUNOTHERAPEUTIC AGENTS

[75] Inventors: Ryota Yoshimoto, Kawasaki; Nobukazu Kashima, Kanagawa; Junji Hamuro, Kanagawa; Koji Mitsugi, Kanagawa, all of Japan

[73] Assignee: Ajinomoto Company, Incorporated, Tokyo, Japan

[21] Appl. No.: 873,302

[22] Filed: Jun. 9, 1986

Related U.S. Application Data

[63] Continuation of Ser. No. 475,180, Mar. 14, 1983, abandoned.

[30] Foreign Application Priority Data

Mar. 15, 1982 [JP] Japan .................. 57-40369

[51] Int. Cl.$^4$ .................. C12P 21/00; A61K 37/00
[52] U.S. Cl. .................. 514/12; 514/8; 514/12; 435/68; 435/70; 530/351; 530/370; 530/371
[58] Field of Search .................. 435/68, 240, 172, .3, 435/70, 948; 514/12, 2, 8; 424/85, 101; 530/351, 417, 828, 370, 371

[56] References Cited

U.S. PATENT DOCUMENTS 4,350,687  9/1981  Lipton et al. .................. 424/177
4,359,389 11/1982  Heine .................. 210/644
4,368,148  1/1983  Bohn .................. 260/112 B
4,390,623  6/1983  Fabricius et al. .................. 435/68
4,406,830  9/1983  Fabnicius et al. .................. 435/68
4,411,992 10/1983  Gillis .................. 435/68

OTHER PUBLICATIONS

Smith et al. *T. Exp Med* vol. 151 p. 1551, 1980 "The Functional Relationship of the Interleukins".
Itamuro et al. *Immrol*, vol. 3y p. 551, 1980 "Induction of Cytotoxic Penduncal Cell by 7-Cell Immune Adjuvarto of the Beta (1→3) Glucan-Type, Lentinunandito Analogues".
Freuhauf et al. *Immunephamucology*, vol. 5, pp. 65–74, 1982 "The Effect of Lentinan on Production of Interleukin by Human Monocytes".
Kashima et al (Including T. Hayami and M. Izawa) *Int. T. Imminopharmacol* 1982 p. 269.
Mier et al. *T. Imor* vol 128 No. 3 Mar. 1982 pp. 1122–1127 "The Purification and Properties of Human 7 Cell Growth Factor".

Primary Examiner—Thomas G. Wiseman
Assistant Examiner—Robin Lyn Teskin
Attorney, Agent, or Firm—Oblon, Fisher, Spivak, McClelland & Maier

[57] ABSTRACT

An immunopropylactic and immunotherapeutic agent comprising human interleukin 2 of human cellular origin is disclosed along with a method of producing the agent.

1 Claim, 5 Drawing Sheets

IMMUNOPROPHYLACTIC AND IMMUNOTHERAPEUTIC AGENTS

This application is a continuation of application Ser. No. 475,180, filed Mar. 14, 1983, abandoned.

BACKGROUND OF THE INVENTION

The present invention relates to immunoprophylactic and immunotherapeutic agents comprising human interleukin 2 produced, e.g., by eucaryote cells including human lymphocytes, cloned human lymphocytes, transformed (malignant) human cell lines, and human T cell hybridomas and by procaryote cells possessing recombinant DNA against neoplastic dieases; bacterial, parasitic and viral infections; and immune disorder diseases such as immune deficiency and autoimmune diseases.

BRIEF DESCRIPTION OF THE PRIOR ART

Interleukin 2 (hereinafter referred to as "IL-2"), formerly referred to as T cell growth factor, is a soluble protein (generally known as "lymphokine") and is produced from T cells activated with a lectin or an antigen (Morgan D. A., et al., Science 1983, 1007–1008 (1976), Gillis, S. et al., J. Immunol., 120, 2027–2033 (1978). Interleukin 2 (IL-2) is capable of modulating lymphocyte reactivity and promoting the in vitro long-term culture of antigen specific effector T-lymphocytes (Gillis, S. et al., Nature 268, 154–156 (1977)). IL-2 is also known to manifest other relevant biological activities such as enhancement of thymocyte mitogenesis (Chen, B. M. et al., Cell. Immunol., 22, 211–224, (1977), Shaw, J. et al., J. Immunol. 120, 1967–1973, (1978)), induction of cytotoxic T cell reactivity (Wagner, H. et al., Nature, 284, 278–280, (1980)) and anti SRBC plaque forming cell responses (Gillis, S. et al., J. Exp. Med., 149, 1960–1968, (1979)) in cultures of nude mouse spleen cells. Accordingly, this lymphocyte regultory substance is useful in potentiating humoral and cellular immune responses and in restoring an immune deficient state to a normal humoral and cellular immune state. These identified immunological activities of IL-2 indicate that IL-2 is useful for medical immunotherapy against immunological disorders including neoplastic diseases, bacterial or viral infections, immune deficient diseases, autoimmune diseases, etc. (Papermaster, B. et al., Adv. Immunopharm. 507, (1980)). Like interferons, IL-2 has been shown to augment natural killer cell activity.

IL-2 has been produced in the prior art by stimulating mouse, rat or human lymphocytes with a mitogen (Gillis, S. et al., Nature, 268, 154–156, 1977, Farrat, J. et al., J. Immunol., 121, 1353–1360, (1978), Gillis, S. et al., J. Immunol., 120, 2027–2033, 1978)) or by stimulating human peripheral blood mononuclear lymphocytes with a mitogen (Gillis, S. et al., J. Immuno., 124, 1954–1962, (1980)). Gillis et al. reported the preparation of murine IL-2 from murine T cell lymphoma cell line (Gillis, S. et al, J. Immunol., 125, 2570–2578 (1980)) and the preparation of human IL-2 from a human leukemia cell line (Gillis, S. et al., J. Exp. Med., 152, 1709–1719, (1980)).

In recent years, immunotherapy has become more and more important in the field of applied medicine. For instance opportunistic infections are frequently observed in newborn children with functional immunodeficiency, cancer patients, patients transplanted with bone marrows, patients receiving chemotherapeutic agents or steroids, and aged patients. Antibiotics so far used in these field against infections do not exert significant effect in immune-deficient or immuno-depressed patients. The situation is almost the same in viral infections, and effective chemotherapeutic agents against viral infections has not been so far provided for clinical uses. Interferon has been reported to have some effects agnast viral infections; however, the nature of the interferons is still unclear and there is uncertainty as to the action modes. Therefore, interferon has not yet been confirmed for its effectiveness. The uncertainty of the effectiveness of interferon is also due to the fact that human interferon does not function in animal model. The presence of species-specificity may one of the major difficulty for the development of interferon as therapeutic agents.

In the field of cancer, the situation of the development of effective therapeutic drugs is analogous to those in infectious diseases and viral diseases. In cancer patients, the prominent depression of immunological function of the host has been widely confirmed, and therefore immunotherapy and immunochemotherapy (adjuvant therapy) have drawn much attention as new definite methods to treat cancer patients. Immunotherapy has been said not only to restore or potentiate the specific immune responses against cancer, but also to improve the general function of host including immunological functions. So far several immunomodulators have been applied in clinics, however almost all of these share the nature of chemotherapeutic agents in such a manner that they also exert direct cytocidal effects against neoplastic cells.

Therefore, the immunotherapeutic agent, which was confirmed for its clinical effectiveness in phase III clinical test, known so far only as antitumor polysaccharide, Lentinan, was discovered and developed by the present inventors and coworkers. Lentinan exerts its antitumor effects by augmenting the reactivity of pre-effector cells to several kinds of lymphokines including interleukin 2.

On the other hand, many of the immuno-modulators now undergoing development frequently show detrimental side effects, such as with B.C.G. and *Corynebacterium parvum*. In this context it is most hopeful in the field of immunotherapy to develop drugs of human-host origin possessing the human characteristic and specific actions.

Furthermore, almost all of the immunomodulators now undergoing development, mainly activate macrophages, act in a nonspecific manner against cancer. However, T lymphocytes play a key role in the induction of specific immune response against not-self and altered-self cells both as regulator cells and effector cells.

Human interleukin 2 comprising the present invention possesses the relevant role for the activation and proliferation of T lymphocytes as described later in in vitro experiments. In vivo effects of human IL-2 in animal model have not been so far clarified at all. So far several reports describe the immunological actions of murine IL-2 preparations containing other functionally active lymphokines and/or monokines in animal models. Thus the reported immunological-biological activities cannot be clarified whether those activities are surely due to purified murine IL-2 or not.

Furthermore in vivo effects of human IL-2 in animal models have not been investigated in terms of its action, immunological activities and therapeutic effects. Murine IL-2 is known to be different from human IL-2 in its chemical and physico-chemical nature such as molecular weight, isoelectric point and so on.

Subsequently so far human IL-2 is unknown for its therapeutic and prophylactic effects against any kinds of diseases. According to the report by Sakurai, Y. et. al., Iyakuhin Kenkyu, 11, 746 (1980) "The methods of evaluation of the effects of immunotherapeutic agents against cancer", it is clearly described that the presence of general immunological activities does not mean the presence of therapeutic effects in the agents.

Generally speaking, several antigens or immunogens containing the antigens are also used as vaccines in active immunotherapy. However the active immunotherapy does not function when the immunological functions of the host are depressed or defective such as in cancer, infections and viral diseases. In order to augment humoral immune responses, the administration of γ-globulin together with the vaccines might be useful. However, when cell-mediated immunity play key roles, the methods is not practical. In such cases, lymphokines such as IL-2 might be useful when used in combination with vaccines such as tumor specific antigens instead of γ-globulin in the augmentation of humoral immune responses.

BRIEF DESCRIPTION OF THE PREFERRED EMBODIMENT

The present inventors analysed the detailed action mode of T-cell-oriented immune adjuvant Lentinan and found that efficient immune regulation can be achieved by modulating the reactivity of immune effector precursor cells to lymphokines, when combined with the administration of lymphokines as the first signal. Triggering of the induction of immune effector cells activation in such a way results in prominent therapeutic effects against various types of immunological diseases. The present inventors have already established methods for producing sufficient amount of purified human IL-2 from eucaryote cells or from procaryote cells possessing recombinant DNA. Thus-obtained purified human IL-2 does not contain any trace amount of other biologically-immunologically active substances such as lymphokines and monokines. Subsequently, the inventors confirmed for the first time the therapeutic effects and immunological activities of purified human IL-2 in animal models, which may provide a human IL-2 as a therapeutic and prophylactic drug to open a new way against various immunological diseases.

The mammalian cells capable of producing IL-2, which are the source of human IL-2 of the present invention, may be T-lymphocytes, such as peripheral blood mononuclear cells, tonsil cells, spleen cells or the like, which are operationally obtainable from mammals. The cells may be conventionally pretreated such as with a nylon column, with an antiserum-complement, by density gradient fractionation, by multiple enzyme treatment such as a combination of neuraminidase and galactose oxidase, by X-ray irradiation or with trypsin to confer the cells with the IL-2 productivity or to increase the IL-2 activity. Also cloned T lymphocytes, obtained from the said mammalian cells after cultivation in the presence of T cell growth factor, may be also used as a source of human IL-2 and are the preferred T lymphocytes. Transformed lymphocyte cell lines such as T lymphocyte-derived leukemia or lymphoma cell line per se or their derivatives obtained by pretreatment or mutation by the methods mentioned above, or the cloned transformed cell lines are preferred as sources of the human IL-2. Evidently, cloned cell lines usually produce larger amounts of IL-2 as compared to parental bulk cell lines. T cell hybridomas, obtained by fusion of the lymphocyte-derived cells mentioned above with the tunor cell lines, such as CEM, Molt 4F, and BW5147, are also preferred mammalian cell lines for use in this invention. In such instance the lymphocyte-derived cell lines include (1) constitutive producers of IL-2 and (2) those which are producers of IL-2 only in the presence of a mitogen introduced into the culture, either in the absence or presence of other IL-2 production co-stimulatory cells.

In order to generate IL-2 in constitutive IL-2 producer cells, the constitutive IL-2 producer cells are cultured under conditions commonly known in the field of cell culture. For the generation of human IL-2 in cells producing IL-2 only in the presence of mitogen, cultured cells are washed extensively with culture medium and resuspended in culture medium, such as Rosewell Park Memorial Institute 1640 (hereinafter "RPMI 1640"), Dulbecco Modified Eagle Medium (hereinafter "DMEM") or in Click's medium, which may or may not contain serum. These culture media may be supplemented with various additives, such as penicillin, streptomycin or other antibiotics, or with fresh L-glutamine, Hepes buffer and sodium bicarbonte in concentrations as are generally used in the field of cell culture.

The preferred cell density may be from 0.5 to $4 \times 10^6$ cells/ml. To induce production of IL-2, appropriate stimulants are added. Suitable such stimulants include mitogens, neuraminidase, galactose oxidase, zinc derivatives such as zinc chloride, or lymphocyte activating substances originated from microorganisms, such as protein A or streptomycin-O. The stimulated cells are recovered and washed. The co-presence of macrophages or dendritic cells during the mitogen stimulation may also increase the amount of IL-2. Likewise the co-presence of cell lines derived from B lymphocytes or B lymphocytes lines, such as Raji, Daudi, K562, and BALL-1 may increase the amount of IL-2 produced.

To propagate the mammalian cells, they are maintained in an in vitro cell culture or in histocompatibility matched animals, under normal conditions. When in vitro culture maintenance is used, the cells may be grown in any of the culture media as were previously found to foster growth of T cells. These culture media may or may not be supplemented with mammal serum, a serum component of serum albumin. During the course of the activation of IL-2 producing cells, phorbol esters, such as PMA or TPA may preferably utilized in a concentration from 10 to 50 ng/ml to boost the level of activation.

The above described process for production of IL-2 may be carried out at temperatures ranging from 32° to 38° C. in a humidified atmosphere and in a pH of approximately 7.0 to 7.4. Furthermore, human IL-2 produced by a living cell line (eucaryotic or procaryotic) possessing the recombinant DNA carrying the gene coding for IL-2 polypeptides is also included in this invention as far as its biological activities coincide with those described later.

The IL-2 produced extracellulary is recovered by any known method, such as precipitation with ammonium sulfate, dialysis to remove salts (under normal or vacuum pressure), gel filtration, chromatography, preparative flat-bed iso-electric focusing, gel electrophoresis, high performance liquid chromatography (hereinafter "HPLC"), (ion exchange, gel filtration and reverse phase chromatography), and affinity chromatography on dye-bound carrier, on activated Sepharose 4B coupled with monoclonal antibody against said IL-2 or on lectin-bound Sepharose 4B and the like. Methods of recovery and partial purification of IL-2 are described in Watson et. al., J. Exp. Med., 150, 849–861 (1979), Gillis et. al., J. Immunol., 124, 1954–1962, (1980), Mochizuki et. al., J. Immunol Methods 39, 185–201, (1980), and Welte, K. et. al., J. Exp. Med., 156, 454–464 (1982).

Human IL-2 used in this invention may be purified and isolated according to the following procedures. The culture supernate or the extract of procaryote cells is brought to 70–85% saturation with ammonium sulfate, after concentration using hollowfibre HIP5 (Amicon DC2), if necessary. The resultant precipitates are collected by centrifugation and the precipitated proteins were dissolved in 0.1M Tris-HCl buffer (pH 7.7) containing 0.2M NaCl and absorbed to CPG (pore size 350 Å, 120–200 mesh, Electro Nucleonics). Human IL-2 activity is eluted with 0.1M Tris-HCl buffer (pH 7.7) containing 0.75M potassium thiocyanate. The eluant containing IL-2 activity is brought to 75–85% saturation with ammonium sulfate and the precipitates are collected by centrifugation. The precipitates are dissolved in a 0.07M sodium acetate buffer (pH 6.0) and dialysed extensively. The dialysate is then centrifuged and the supernatant is applied to CM-Sephadex C-25 (Pharmacia). Human IL-2 activity is eluted from the column with 0.5M sodium acetate buffer (pH 6.0) and the eluant is brought to 80% saturation with ammonium sulfate. The collected resultant precipitate is dissolved in a minimum volume of 0.5M sodium phosphate buffer (pH 7.0) containing 1.25M NaCl. The IL-2 preparation is then applied to gel filtration using sephadex G-75 superfine (Pharmacia) equilibrated with 0.05M sodium phosphate buffer (pH 7.0) containing 1.25M NaCl and eluted with the same buffer. IL-2 activity is eluted in fractions with a molecular weight of approximately 15,000 daltons. The fractions containing IL-2 activity are collected and adjusted to 1M glucose concentration. The solution is then applied to phenyl Sepharose cL 6B (Pharmacia) equilibrated with 0.05M sodium phosphate buffer (pH 7.0) containing 1.25M NaCl and 1M glucose. At this stage human IL-2 can be purified 2,000 fold with the specific activity of $1.0 \times 10^6$ unit/mg protein and does not contain any trace amount of other lymphokines or cytokines such as monokines, and the preparation can be easily used for the present invention. To obtain completely purified human IL-2 in terms of other proteins contamination, the IL-2 preparation described above is then applied to a reverse-phase HPLC column (e.g. Ultrapore RPSC, Beckmann). Proteins absorbed on the gel can be washed with triethylamine-acetic acid (hereinafter "TEAA") buffer and eluted with a 1-propanol gradient in TEAA buffer. Human IL-2 is strongly bound on the gel and is eluted at about 50% of 1-propanol after most of the contaminating proteins are eluted off. At this stage the human IL-2 shows a single band corresponding to molecular weight 15,500 on SDS-polyacrylamide gel electrophoresis and shows specific activity of around $1-2 \times 10^7$ unit/mg.

The polypeptide thus obtained shows the same biochemical and biological behavior as has been known for IL-2 produced by mammalian cells by mitogen stimulation, and has IL-2 activity (Gillis, S. et. al., Immunological Rev., 54, 81–109, (1981)). The molecular weight is around 15,000 dalton, and IL-2 activity was completely neutralized or precipitated with monoclonal anti-IL-2 antibody in the presence or absence of immunoadsorbents, such as Igsorb (Encyme Center). In immunoelectrophoresis, the IL-2 polypeptide shows only a single precipitate against the corresponding anti-IL-2 antibody. The IL-2 activity remains stable after reduction with 2-mercaptoethanol, and is resistant to treatment with DNAse and RNAse as well as to heat treatment at 56° C. for 30 min. The activity is stable at a pH between pH 2 to 9.

The activity of IL-2 may be ascertained by the microassay procedure principally discussed by Gillis et. al (Gillis, S. et al., J. Immunol., 120, 2027–2033 (1978)). The assay monitors the IL-2 dependent cellular proliferation of a cytotoxic T lymphocyte cell lines (hereinafter "CTLL") generated according to the methods described by Gillis et al. That is, $4 \times 10^3$ CTLL cells are inoculated into 100 μl of RPMI 1640 medium containing 2% FCS in 96-well flat-bottomed microplates together with 100 μl of the serially diluted diluted test samples. After 20 hours incubation at 37° C. in 5% $CO_2$ incubator, cells are pulsed for 4 hours with 0.5 μCi of $^3$H-TdR and harvested onto glass fibre strips with the aid of an automated cell harvester then the incorporated radioactivity is measured by liquid scintillation counting. By these assay procedures, the CTLL cells cultured in the presence of IL-2 were found to incorporate $^3$H-TdR in a dose dependent manner resulting in the definite calculation of the amount of IL-2 contained in test samples.

Thus obtained and characterized human IL-2 can be next extensively investigated for its biological, immunological and therapeutic effects to complete the present invention. Generally speaking, crude IL-2 preparation, containing other lymphokines, monokines and cytokines, is not too useful for clinical use, since it is difficult to establish which is the active entity contributing to its pharmacological effects and therefore it is impossible to define the schedules, doses and routes of administration in practical uses in human.

Human IL-2 used as a therapeutic drug comprising the present invention does not contain any other known lymphokines and cytokines, such as T cell replacing factor, colony stimulating factor, immune interferon, interleukin 1 (hereinafter "IL-1"), macrophage activating factor, lymphotoxin, tumor necrotizing factor, B cell growth factor and so on. The absence of these activities in human IL-2 of the present invention was confirmed according to the functional tests well known in the field. In brief, (1) T cell replacing factor was tested by assaying the activity to generate the plaque forming cells in spleen cells deprived of T cells by anti Thy 1 antibody, (2) colony stimulating activity was tested by assaying the formation of colonies in bone marrow cell culture in methylcellulose, (3) Immune interferon activity was tested by assaying the presence of antivival activity in the preparation, (4) IL-1 activity was tested by assaying the conversion of IL-2 nonproducer LBRM33-1A5 to producer in the presence of the IL-2 preparation for 4 hrs., (5) Macrophage activating factor was checked by assaying the cytostatic activity of macrophages against tumor cells after exposure of macrophages to the IL-2 preparation, and so on.

The present inventors succeeded in isolating and producing on a large scale human IL-2 with defined and characterized nature and function, lacking any other biologically active lymphokines or monokines, and subsequently succeeded in confirming the pharmacological and therapeutic effects in animal models against bacterial, viral and parasitic infections, immune deficient diseases, neoplastic diseases and autoimmune diseases, all of which accompany the immunological disorders. Thus the present invention newly established provides relevant and useful immunotherapeutic drug possessing prophylactic and therapeutic effects against a wide range of immunologically disordered diseases. The human IL-2 comprising the present invention promotes the growth of activated or antigen primed T lymphocytes (monoclonal functional T cells), and thus the pharmacological effects against diseases accompanying the disorders of T lymphocytes function can be most important.

The pharmacological effects found in the human IL-2 comprising the present invention are as follows: (1) the promotion of the growth of a long term cultured cytotoxic T lymphocyte cell line against murine tumor cell FBL-3, (2) the promotion of the growth of allo-killer T lymphocytes generated in mixed lymphocytes or in mixed lymphocyte-tumor culture in histocompatibility incompatible combination and of hapten-specific, H-2 restricted killer T lymphocytes, and the induction of killer activity from the memory state of these killer T cells in the absence of antigen, (3) augmentation of natural killer cells (hereinafter "NK cells") activity during in vitro culture of splenic cells, (4) synergistic augmentation of NK cells activity with interferon or interferon inducers during in vitro culture of splenic cells, (5) synergistic augmentation of NK cells activity during in vitro culture of splenic cells with in vivo Lenitinan administration, (6) Augmentation or restoration of the inducibility of killer T lymphocytes from splenic T lymphocytes (used as responder cells) originated from immune function depressed mice bearing syngeneic tumors, (7) Augmentation or restoration of NK cells activity of splenic cells of NK cells activity depressed mice bearing syngeneic tumors, and (8) Induction of allo-killer T lymphocytes in the absence of Ia$^\pm$ macrophages in the mixed lymphocytes culture between H-2 incompatible spleen cells, where allo-killer T lymphocytes cannot be generated usually.

The above-illustrated pharmacological effects clearly shows that the human IL-2 comprising the present invention is distinct from other lymphokines, is capable of promoting the growth and differentiation of T lymphocytes, is capable of augmenting the induction of cytotoxic T lymphocytes (hereinafter "CTL") and NK cells playing key roles as immune effectors, is capable of exerting synergistic effects in the induction of immune effectors with Lentinan, interferon and interferon inducers, and is capable of restorating the induction of immune effectors even from the lymphocytes originated from immune depressed hosts. The fact that the human IL-2 not only shows diverse immunological activity, but also augments or restorates the activation of CTL and NK cells clearly demonstrates that the human IL-2 comprising the present invention is significantly useful for phophylaxis and therapy of immunological diseases.

The biological and immunological effects found by in vivo administration of human IL-2 comprising the present invention are as follows: (9) Augmentation of NK cells activity by administration either with interferon, interferon inducers or solely, (10) Augmentation of the allo-killer T cells induction, (11) Augmentation of CTL induction in mice bearing syngeneic tumors by administration either with Lentinan, picibanil or solely, (12) Augmentation of cell mediated immune responses measured by delayed type hypersensitivity using antigens such as sheep red blood cells (hereinafter "SRBC"), (13) Augmentation of tumor specific immune responses measured by delayed type hypersensitivity against tumor associated transplantation antigens, (14) Restoration of cell mediated immune responses in immune depressed mice bearing syngeneic tumors, measured by CTL induction, NK cells activation and delayed type hypersensitivity, and (15) Induction of anti SRBC antibody forming cells and CTL in nude mice defective in intact T lymphocytes functions.

The effects described as in vivo effects of the human IL-2 comprising the present invention clearly demonstrate for the first time that human IL-2 is able to exert immunological activity even by in vivo application in animal models, although the absorption, decomposition and metabolism of IL-2 in animal host have been completely unknown. In summary the human IL-2 comprising the present invention shows also in vivo as was observed in vitro the capability to promote the growth and differentiation of T lymphocytes, to augment the induction of CTL and NK cells relevant as immune effectors, and to restore these immunological functions even in a host accompanied depression, defect and deficiency in immune reactivity.

Based on these findings human IL-2 was firstly clarified to be useful by in vivo application for prophylaxis and therapy of immunological diseases. Above all the most important are the findings that in vivo application of human IL-2, in animal model, certainly augments the induction of CTL as specific immune effectors and augments the activity of NK cells functioning as non-specific immune effector cells. It is well known that various immunological functions are depressed in aged hosts. Recently Gillis, S. et al., (J. Clin. Invest., 67, 937, (1980)) discuss the depression of IL-2 production in aged hosts. The finding described above demonstrates the availability of the human IL-2 comprising the present invention as a therapeutic drug widely for the improvement of immunological function. In addition, synergistic pharmacological effects of human IL-2 with interferon, interferon inducer, lentinan and with other immune-modulators were also invented for the first time. Furthermore, the in vivo augmenting effect of human IL-2 comprising the present invention of cell mediated immune responses against antigens as immunogens or against tumor specific antigens clearly demonstrate the in vivo adjuvant effects when administered together with an antigen as an immunogen, indicating the usefulness of the human IL-2 as a drug in active immunotherapy against wide range of diseases. The inventors finally confirmed the therapeutic effects in animal models of human IL-2 comprising the present invention. As is evident from the findings previously illustrated from (1) to (15), the availability of the human IL-2 comprising the present invention as a drug is not limited to the scope illustrated in the followings, but includes those diseases immunologically related within a wide and equivalent range of conditions and the like without affecting the spirit or scope of the invention or of any embodiment thereof.

The confirmed therapeutic effects are as follows, (1) Prolongation of survival time of mice after resection of syngeneic tumors, (2) Prolongation of survival time of mice bearing syngeneic tumors when IL-2 was administered together with cyclophosphamide or FT207, (3) Prolongation of survival time of mice bearing syngeneic tumors when IL-2 was administered with tumor vaccines, (4) Prolongation of survival time of mice bearing syngeneic tumors and the growth inhibition of syngeneic tumors when IL-2 was administered solely, (5) Prolongation of survival time of mice suffering from bacterial infection, (6) Prolongation of survival time of mice suffering from viral infection, (7) The synergistic growth inhibition of syngeneic tumors with lentinan administration, (8) Prolongation of survival time of autoimmune MLR (1pr/1pr) mice.

These in vivo therapeutic effects in animal models of the human IL-2 comprising the present invention surely demonstrate the possible availability of the drug in practice in clinics against a wide range of diseases related to immunological disorders.

The human IL-2 comprising the present invention should possesses the specific activity more than $2 \times 10^5$ units/mg protein to avoid any kind of reverse effects or detrimental side effects. According to the kind of diseases, to the condition of the patients and to the immune state, the amount of the drug administered and the frequency of administration as well as administration routes and vehicles should be determined although in the following examples only intravaneous injection is illustrated. Human IL-2 having a specific acitivity lower than that indicated above or human IL-2 contaminated with other lymphokines or monokines may be included in the present invention, because it will be understood by those of skill in the art that the same can be performed within a wide and equivalent range of conditions, without affecting the spirit or the scope of the present invention.

The present invention was achieved by finding in vivo pharmacological, therapeutic and prophylactic effects detailed in the art, and therefore the drugs containing any other kinds of components not interfering with the in vivo effects of the human IL-2 comprising the present invention may also be included in the present invention.

EXAMPLE 1

Production of Human IL-2

Human peripheral blood T lymphocytes were harvested from peripheral blood by well known procedures in this field and suspended at the cell density of $1 \times 10^6$/ml, to which the same volume of a suspension of Raji cells, a human B lymphocyte-derived cell line, was added at a cell density of $1 \times 10^6$/ml. Then 25 μg/ml of Concanavalin A (Con A) and 10 ng/ml of Phorbol myristate acetate (PMA) in a final volume of 2000 ml were added. This cell suspension was incubated in a 10 l jar fermentor at 37° for 48 hrs, and the IL-2 containing culture supernatant was obtained by removing the cells and their debris by centrifugation. The medium for the above IL-2 production was Rosewell Park Memorial Institute (RPM1)-1640 containing 1% fetal bovine serum. Culture supernatant obtained as above contained 36 μ/ml of IL-2, where "unit" is abbreviated as "u".

On the other hand, an established cell line of human T cell leukemia, J-111 (ATCC CRL 8129), was suspended at a cell density of $4 \times 10^6$/ml in 1000 ml of 0.5% bovine serum albumin (BSA)-containing RITC-55-9 medium (serum-free medium), and then Con A was added at a final concentration of 10 μg/ml. This cell suspension was incubated in Roller Bottle (Falcon Co.) without air supply (under the air-closed condition) in the Roller incubator at 37° for 24 hrs. In the supernatant obtained by centrifugation after the incubation was over, the activity of IL-2 was 4096 u/ml.

At the same time, the activities of IL-2 produced by Jurkat-FHCRC line and Jurkat-71886 under the same condition were found to be 64 and 28 u/ml, respectively.

Further, cloned T lymphocytes which were obtained by culturing human peripheral blood lymphocytes in the presence of T cell growth factor, and a T cell hybridoma which was obtained by hybridizing human T lymphocytes with human T cell leukemia cell line, CEM, were stimulated by Con A under the same condition as the above and found to give 24 and 12 u/ml of IL-2 activity, respectively.

IL-2-containing culture supernatant obtained from Jurkat-III cell line was first concentrated to ten-fold by using a hollow fiber ultra filtrating concentrator HIP5 (Amicon Co; Type DC2). This concentrate was salting out by adding ammonium sulfate at a final concentration of 85%, then passed through a Sephadex G-15 (Pharmacia Co., Sweden) column to remove the salts, followed by passing through DEAE-cellulose column and by eluting stepwise under the varied ionic strength. IL-2 activity-containing fractions eluted by 0.06M Tris-buffer (pH 7.6) were pooled, and were then lyophilized to dryness and chromatographed on controlled-pore-glass beads column, followed by eluting with 0.3M glycine-HCl buffer. IL-2 activity-containing eluates were pooled and adsorbed on orange-sepharose column in the presence of 0.01M Tris buffer (pH: 7.6) and again eluted by 0.01M Tris-buffer-1.0M NaCl. IL-2 activity-containing solution thus obtained was dialyzed against 50 mM ammonium bicarbonate, and ammonium bicarbonate was removed by freeze-drying. This obtained fraction was subjected to preparative electrophoresis on apparatus FBE 3000 (Pharmacia Co., Sweden), and the gel plate developed was cut into 30 pieces, from which protein was extracted with and lyophilized against sterilized distilled water. Finally, human IL-2, after IL-2 activity and the amount of its protein were determined, was obtained for the present invention.

The above purification procedures is summarized in Table 1.

TABLE 1

| | IL-2 grade | Purification of IL-2 | | | |
|---|---|---|---|---|---|
| | | Vol (ml) | IL-2 activity (u/ml) | Total activity (units) | Specific activity (units/mg protein) |
| (A) | Culture supernatant | 10000 | $4.1 \times 10^3$ | $4.1 \times 10^7$ | $1.5 \times 10^2$ |
| (B) | Fractions from DEAE chromatography | 500 | $9.2 \times 10^4$ | $4.6 \times 10^7$ | $6.2 \times 10^3$ |
| (C) | Eluates from CPG | 50 | $5.5 \times 10^5$ | $2.8 \times 10^7$ | $9.1 \times 10^4$ |
| (D) | Eluates from orange sepharose | 10 | $2.7 \times 10^6$ | $2.7 \times 10^7$ | $3.6 \times 10^5$ |
| (E) | Active fractions after isoelectric focusing | 10 | $1.1 \times 10^6$ | $1.1 \times 10^7$ | $8.2 \times 10^5$ |

IL-2 preparation obtained in grade E did not show any toxicity even after i.v. injection in amounts of $10\times10^6$ unit per mouse. At the same time, $10^5$ u/ml of IL-2 of grade E did not show any cytocidal against human L cell in vitro, while IL-2 preparation in grade A and C did inhibit the in vitro growth of the above L cells at a concentration of $10^5$ u/ml, which showed these IL-2 preparations contained some directly cytotoxic substances against the cells.

EXAMPLE 2

Enhancing effect of IL-2 on in vitro growth of T lymphocytes

One ml of activated T lymphocytes CTLL suspension, $1\times10^4$/ml in its cell density, was added in each well of a 24-well Nunc culture plate, to which 10 μl of IL-2 sample was added, and then an increase in cell number of T lymphoctyes was observed in every 24 hours, where these lymphocytes were cultured in RPM1-1640 containing 5% of fetal calf serum at 37° C. in $CO_2$ (7.5%) incubator. After the cells were stained with Eosin, viable and dead cells were enumerated under the microscope. Experimental results are shown in FIG. 1A.

Figure 1B:
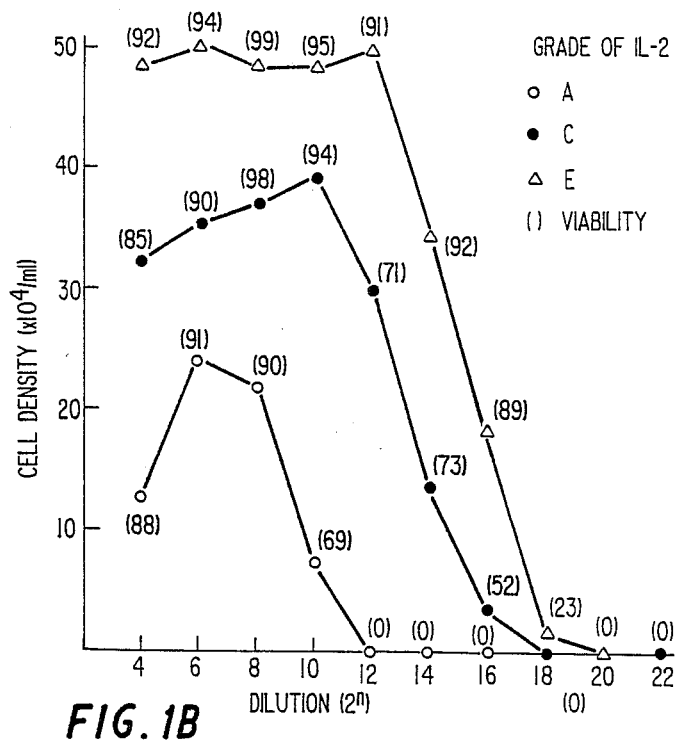

Further, CTLL cell suspension was added into RPM1-1640 medium at a cell density of $1\times10^4$/ml, and serially diluted IL-2 sample at $2^n$ was added in amount of 100 μl/ml. After 96 hrs cultivation, the growth of CTLL in 1 ml/well of a 24-well cutlure plate (Nunc Co.) was followed by staining the cell with Eosin and by observing viable and dead cells under the microscope, as shown in FIG. 1B. As shown, partially purified IL-2 sample was found to contain an inhibitory activity against CTLL. IL-2 grades given in FIGS. 1A and 1B are the same as shown in Table 1.

EXAMPLE 3

Augmenting effects of IL-2 on the in vitro induction of Killer T lymphocytes from memory killer T lymphocytes Splenocytes, $4\times10^6$ cells, from CBA/J mice and splenocytes ($1\times10^6$ cells) which were X-ray irradiated at 2,000 R and from BALB/C mice, were suspended in 2 ml of click medium containing 5% FCS and cultured in 24-well Nunc culture plate for 10 days. Then memory cells of allo-killer T lymphocytes were prepared, in which killer activity was not detected in these memory cells.

Thus obtained memory cells were added at a cell density of $5\times10^4$ cells per well of 96-well micro culture plate, and serial dilutions at $2^n$ of IL-2 samples were added at a final volume of 200 μl in Click medium in the same plate, which were incubated at 37° in 5% $CO_2$ incubator for 3 days.

Figure 2:
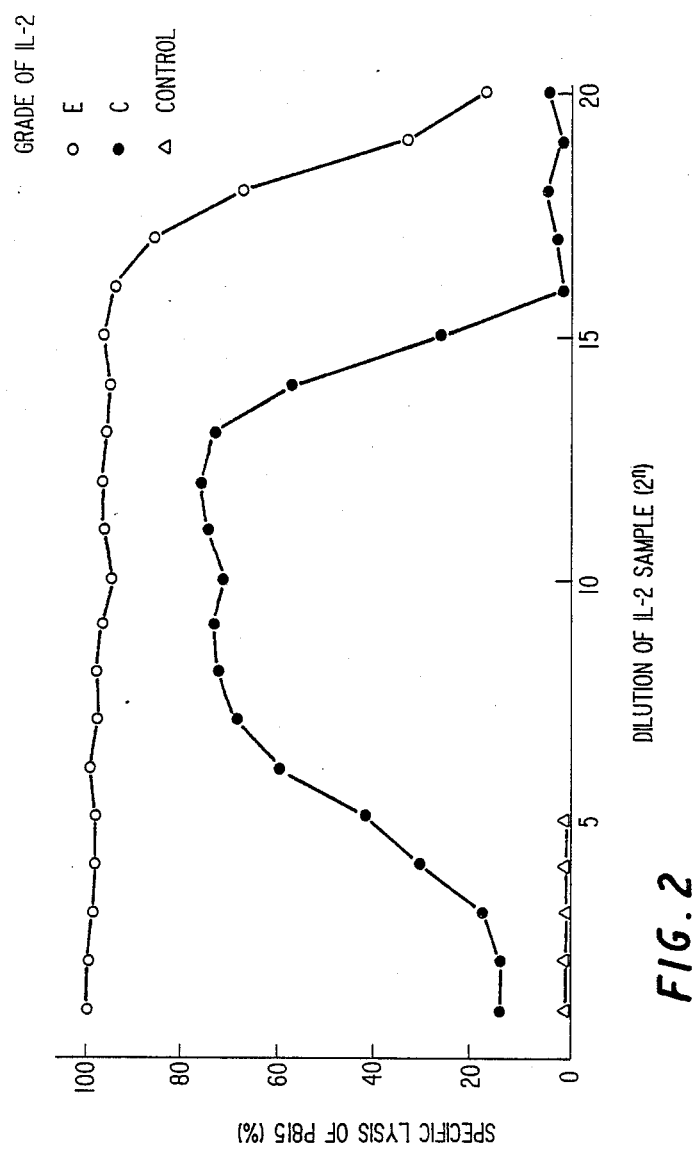

After washing the cells, fresh medium and $^{51}$Cr-labelled mastocytoma P815-$X_2$ at a cell density of $1\times10^4$/well were added, followed by incubating for 3 hrs at 37° in 5% $CO_2$ incubator. Then lysis of P815-$X_2$ target cells were followed by counting the amounts of $^{51}$Cr released from target cells in auto gamma counter, and the effects of IL-2 on the induction of killer T lymphocyte from memory cells were obtained, as shown in FIG. 2. The grade of IL-2 was the same as that shown in Table 1.

EXAMPLE 4

Augmenting effects of natural killer activity in vitro and combination effects with lentinan and interferon Splenocytes were prepared as single cell suspensions as usual from C3H/HeN mice in Dulbecco modified Egle medium (DMEM) at a cell density of $10^7$ cells/2 ml, which were added in 24 well culture plate (Nunc Co.). IL-2 preparation, 100 μl, was added in each well, and the mixtures were incubated at 37° for 24 hrs in 5% $CO_2$ incubator. Thus prepared cells were resuspended in 2 ml of fresh medium, and 1 ml each of cell suspension was added to small test tube, to which $2\times10^4$ cells of $^{51}$Cr-labelled YAC-1 cells were added. After 4 hrs incubation, the amounts of $^{51}$Cr released into the supernatant were assayed, by auto gamma counter, to determine the specific lysis of YAC-1 cell, as target cell; in another words, to know the activation of natural killer activity.

The effects of IL-2 in collaboration with lentinan were demonstrated by using splenic cells derived from C3H/HeN mice, to which lentinan (1 mg/kg) was administered by i.v. injection 24 hours before their splenic cells were taken out.

Figure 3:
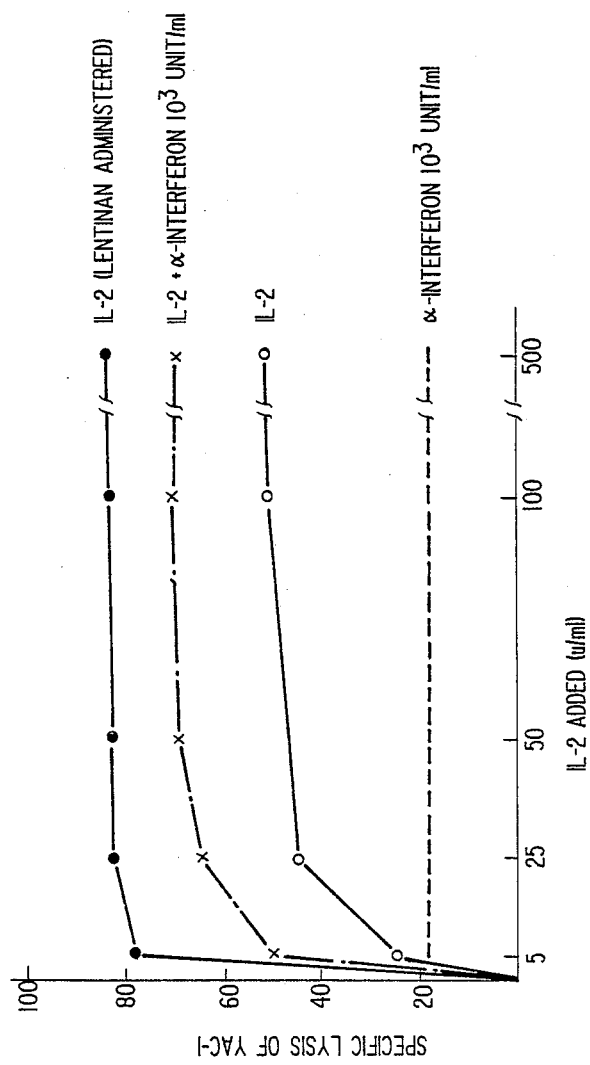

The effects of IL-2 in collaboration with α-interferon were determined by adding $10^3$ iu/ml of α-interferon together with IL-2 to the Nunc assay plate, as shown in FIG. 3, where IL-2 preparation employed was grade E mentioned in Table 1.

EXAMPLE 5

Augmenting effect on NK activity in vivo and its collaborative effect with lentinan IL-2 preparation (0.1 ml) was intravenously injected into the tail of C3H/HeN mice. Splenocytes were harvested from said mice on the 3rd day after IL-2 injection and suspended in DMEM at a cell density of $2\times10^6$ cells/ml. At the same time, $^{51}$Cr labelled YAC-1 cells ($2\times10^4$/100 μl) were added Then augmenting effects of IL-2 on NK activity were determined by $^{51}$Cr release-experiment as mentioned in Example 4.

Collaborative effects with lentinan were determined by starting with the i.p. injection of lentinan (1 mg/kg) one hour before IL-2 administration into the same mice.

TABLE 2

| Augmenting effects of IL-2 on NK activity (in vivo) | | | |
|---|---|---|---|
| Amounts of IL-2 injected (units/head) | Administration of lentinan (1 mg/kg) | Cytotoxicity against YAC-1 | |
| | | E* | C* |
| control (saline) | control (saline) | 22.3 | 22.3 |
| control (saline) | + | 44.6 | 44.6 |
| 5 | − | 48.2 | 30.1 |
| | + | 62.3 | 48.3 |
| 25 | − | 64.2 | 45.3 |
| | + | 80.3 | 57.2 |
| 100 | − | 72.2 | 23.1 |
| | + | 81.3 | 40.8 |

*shows the grade of IL-2 preparation employed in this Expt. (Ref. Table 1)

EXAMPLE 6

Augmenting effects of IL-2 on the in vivo killer T lymphocyte induction and its collaborative effects with lentinan C 57 BL/6 mice were i.p. injected with P815-$X_2$ mastocytoma cells suspended at $1\times10^6$ cells/0.5 ml of saline. 100 μl of IL-2 each was intravenously injected to their tail on the 3rd day and the 5th day, followed by harvesting splenocytes on the 10th day. These splenocytes, as effector cells, and $^{51}$Cr-labelled P815, as target cells, were mixed at the ratio of 100:1, and augmenting effects of IL-2 on killer T lymphocyte activation were determined by assaying the amounts of $^{51}$Cr released from target cells. As shown in Table 3, in the IL-2-administered group marked augmenting effect was observed, comparing with the control group which was administered with saline instead of IL-2 preparation. In addition, this augmenting effect was further enhanced by the administration of lentinan (0.1 mg/kg) on day 1.

TABLE 3

Augmenting effects of IL-2 on the induction of Killer T lymphocytes (in vivo)

| Amounts of IL-2 injected (units/head) | Administration of lentinan (0.1 mg/kg) | Cytotoxicity against P815 E* | Cytotoxicity against P815 C* |
|---|---|---|---|
| control (saline) | control (saline) | 25.2 | 25.2 |
| control (saline) | + | 42.3 | 42.3 |
| 5 | — | 38.6 | 17.3 |
|   | + | 70.4 | 20.6 |
| 25 | — | 60.3 | 26.4 |
|   | + | 80.4 | 40.3 |
| 100 | — | 80.6 | 30.2 |
|   | + | 82.3 | 40.4 |

*shows the grade of IL-2 preparation employed in this experiment (ref. in Table 1).

EXAMPLE 7

Augmenting effects of IL-2 on the induction of (syngeneic) killer T lymphocytes against syngeneic tumor by administering IL-2 into syngeneic tumor bearing mouse and collaborative effects with lentinan P815-X$_2$ mastocytoma cells (5×10$^6$/0.1 ml) were subcutaneously injected into DBA/2 mice. IL-2 preparation (100 units/0.1 ml) was intravenously injected into the tail of these mice on the 18th day after tumor transplantation, and on the 5th day after IL-2 administration Splenocytes and tumor cells were harvested to prepare the single cell suspensions, respectively. Tumor cell fraction was further subjected to Ficol (Pharmacia Co.) density gradient to get lymphocytes in 88% purity.

Splenocytes or lymphocytes were mixed with $^{51}$Cr-labelled P815, as target cells, at the effector/target cell ratio of 100:1 and the mixture was incubated for 4 hours, followed by analyzing the amounts of $^{51}$Cr released from target cells. In other words, the killing activities of splenic T lymphocytes and T lymphocytes obtained from solid tumor against syngeneic tumor were analyzed.

As shown in Table 4, the induction of killer T lymphocytes was observed in the splenocytes and intra tumor lymphocytes only after administration of IL-2 to the syngeneic tumor bearing mice.

TABLE 4

Induction of Killer T lymphocytes against syngeneic tumor

| Amounts[1] of IL-2 administered (units/head) | Administration[2] of lentinan (1 mg/kg) | Cytotoxicity against P815 (%) in Splenocytes | Cytotoxicity against P815 (%) in intra tumor lymphocytes |
|---|---|---|---|
| control (saline) | control (saline) | 0 | 0 |
| control (saline) | + | 6 | 4 |
| 100 | — | 28 | 32 |

TABLE 4-continued

Induction of Killer T lymphocytes against syngeneic tumor

| Amounts[1] of IL-2 administered (units/head) | Administration[2] of lentinan (1 mg/kg) | Cytotoxicity against P815 (%) in Splenocytes | Cytotoxicity against P815 (%) in intra tumor lymphocytes |
|---|---|---|---|
|   | + | 42 | 54 |

[1]IL-2 preparation employed was grade E as shown in Table 1. No inducing activity was observed in the preparation "Grade C" in combination with or without lentinan.
[2]Lentinan was i.p. injected each in amounts of 1 mg/kg on the 15th, 16th and 17th days after P815 transplantation.

EXAMPLE 8

Augmenting effects of IL-2 on tumor antigen-specific cellular immune responses

Syngeneic tumor cells, MM46, were transplanted in amounts of 1×10$^6$ cells/0.1 ml to C3H/HeN, and IL-2 preparation, 100 u/0.1ml saline, was intravenously injected into the tail of this mouse on the 13th day after tumor cell transplantation, in which tumor cells were observed to be growing. On the other hand, tumor antigen was extracted by known procedure from MM46 cells with 3M-KCl.

Figure 4:
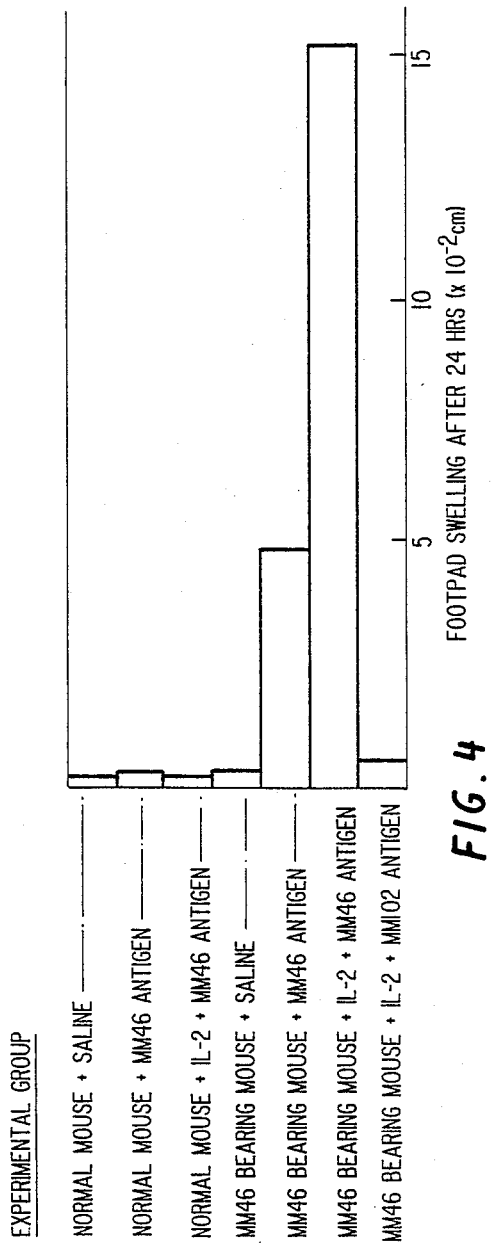

Thus obtained tumor antigen was injected in amounts of 0.60 mg as protein to a foot-pad of a mouse bearing the syngeneic tumor, MM46, on the 20th day after tumor transplantation, or on the 7th day after IL-2 injection, and, in 24 hours, the thickness of the food pad was measured, wherein the augmenting effect of IL-2 on tumor specific delayed type hypersensitivity reaction, which is a specific cellular immune reaction to tumor antigen in syngeneic tumor bearing mouse, was detected. As the controls, the same amount of IL-2 was injected to C3H/HeN without MM46 transplantation and the same amount of antigen prepared from MM102, as equivalent amount of protein to the above experiment, was injected, as given in FIG. 4, wherein IL-2 preparation employed was the grade E, obtained in Table 1. Enhancement of antigen specific delayed type hypersensitivity against MM46 tumor was observed only in the case that IL-2 was administered to MM-46 tumor-bearing mouse, and these data strongly indicated that the administration of IL-2 could augment an antigen specific cellular immune response against the syngeneic tumor in syngeneic tumor bearing mouse.

EXAMPLE 9

Recovery from immune deficient condition in immunosuppressive animals

In order to demonstrate the recovery from various immune responses through the recovery of T lymphocyte functions in the case which IL-2 is administered to an immunosuppressed animal, and IL-2 was injected into a tumor bearing mouse to determine whether the immunosuppressive state was recovered or not. For this purpose, DBA/2 mice were subcutaneously transplanted with P815-X$_2$ mastocytoma (1×10$^6$ cells/0.1 ml) and, at the stage wherein tumor grew enough in size, IL-2 was administered. Then the effects of IL-2 were demonstrated in terms of (i) recovery of NK cell-activation, (ii) recovery of allo-killer T lymphocytes induction and (iii) delayed type hypersensitivity reaction against sheep red blood cells.

(i) NK cell activation

NK cell activation was assayed as follows: IL-2 preparation (50 u/0.1 ml saline) was intravenously injected into the tail of a mouse on the 16th and 18th days after P815-$X_2$ transplantation, and splenocytes were harvested on 20th day after P815-$X_2$ transplantation. The cytotoxicity against YAC-1, as target cells, was determined to measure the amounts of $^{51}Cr$ released from target cells after 4 hrs incubation in the assay mixture containing effector cells and $^{51}Cr$ labelled target cells at the ratio of 200:1.

NK cell activity of normal (non-tumor bearing) mouse was 19.8% in term of specific lysis, but in P815-$X_2$ bearing mice, NK cell activity was depressed as much as 7.6%. Comparing with the above controls, IL-2 was observed to markedly recover the NK cell activity from its immunosuppressive state to the level as much as 22.3% in the experimental group wherein purified IL-2, grade E (as shown in Table 1), was intravenously administered.

The depression of NK cell activation was also observed in the case wherein ascites fluid (0.5 ml) obtained from P815 bearing mice (ascites type) was i.p. injected 3 times (from 19.8% to 6.4% in term of specific lysis), but this depression of NK cell activation was recovered up to 23.4% by IL-2 administration as mentioned above.

(ii) Induction of allo-killer T lymphocytes

Splenocytes were harvested, on the 20th day after P815-$X_2$ s.c. transplantation, from the mouse treated as described in the case (i), and these splenocytes, as responder cells, and splenocytes, as stimulator cells, which were harvested from $C_{57}BL/6$ and X-ray-irradiated (2000R), were subjected to the mixed lymphocyte culture (MLR) to induce allo-killer T lymphocytes under the same condition as described in Example 3. Effector cells were recovered on the 5th day after MLR and mixed with $^{51}C$-labelled EL-4 thymoma cell, as target cells, at Effector/target cell ratio of 10:1. After 3 hours incubation, the activity of allo-killer T lymphocytes was determined as specific lysis (%) against the target, EL-4 cells.

In the splenocytes of normal mice, enough level of allo-killer T lymphocytes induction was detected, but no induction of allo-killer T lymphocytes was observed in the splenocytes derived from P815-$X_2$ bearing DBA/2 mice. While induction of allo-killer T lymphocytes was markedly observed for the administration of IL-2 even in these (the above) immuno-deficient conditions. This finding strongly indicated that IL-2 administration into immuno-deficient animals elicited the recovery of immunological functions from their deficient states, as the results are given in Table 5.

TABLE 5

Effect of IL-2 on the recovery for the induction of allo-killer T lymphocytes from P815 bearing DBA/2 mice

| | Amounts of IL-2 administered (units/head) | | | |
|---|---|---|---|---|
| | control (saline) | 20 | 50 | 100 |
| Specific lysis for EL-4(%) | 0 | 46 | 52 | 54 |

(iii) Delayed type hypersensitivity reaction for sheep red blood cells (SRBC)

Figure 5:
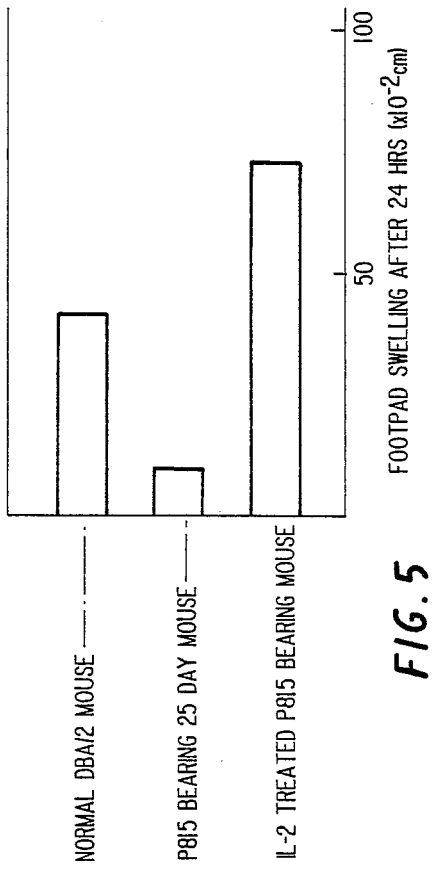

DBA/2 mice were intravenously injected with 50 u/0.1 ml of IL-2 on the 20th day after s.c. transplantation of P815-$X_2$ mastocytoma ($1 \times 10^6$/head), as described in the above case (i), and then were injected into a foot-pad with SRBC ($1 \times 10^6$ cells/head) on the 25th day after P815 transplantation, followed by injecting again with SRBC ($1 \times 10^6$ cells/head) on the 6th day after the above treatment. Then the thickness of the foot-pad elicited by the above treatments was measured. As given in FIG. 5, the depressed-delayed type hypersensitivity reaction in terms of the foot pad reaction in tumor-bearing and immuno-deficient animals was clearly indicated to be recovered or enhanced up to the normal level or more by the administration of IL-2.

EXAMPLE 10

Effects of IL-2 on the appearance of immunological functions in T lymphocytes- or immunological function-deficient animals The following example clearly demonstrates the effects of IL-2 administration on the appearance of immunological functions in nude mice which are deficient in T lymphocyte functions and, therefore, deficient in Killer T lymphocyte induction and the antibody production against T lymphocyte dependent antigen.

BALB/C nu/nu mice were injected at their foot-pads with X-ray irradiated (2,000R) splenocytes ($2 \times 10^7$ cells) from C57BL/6 mice, followed by sensitizing continuously for 2 days with allo-antigen. IL-2 preparation, grade E shown in Table 1, (100 unit/100 μl) was started with i.v. administration, at the same time as antigen administration began, and was further administered 3 times in every 3 days. After 10 days, splenocytes ($4 \times 10^6$ cells) from this BALB/C nu/nu mice were incubated with X-ray irradiated (2,000R) splenocytes ($1 \times 10^6$ cells) from C57BL/6 in 2 ml of Click-RPM/medium for 5 days, and the induction of killer activity against $^{51}Cr$-labelled EL-4 cells, as target cells, was determined. As given in Table 6, by the administration of IL-2, Killer T lymphocytes were induced in nude mice deficient in T cell functions.

TABLE 6

Induction of Killer T lymphocytes by in vivo administration of IL-2 (Specific lysis against target cells %)

| IL-2 administration | Effector/target cell ratio | | | |
|---|---|---|---|---|
| | 500:2 | 100:1 | 20:1 | 4:1 |
| − | 2 | −1 | −2 | 1 |
| + | 48 | 21 | 12 | 2 |

Mouse: BALB/C nu/nu
Antigen: C57BL/6 spleen cell
IL-2: Sample E shown in Table 1
Target cell: EL-4
IL-2 administration: 100 u/100 μl × 3 times BALB/C nu/nu mice were injected (i.p.) with SRBC ($1 \times 10^6$ cells) as antigen, and, at the same time, intravenously administered with IL-2 sample E (100 u/100 μl), followed by i.v. injection of IL-2 3 times in every 3 days. Then the splenocytes ($0.75 \times 10^6$ cells) from BALB/C nu/nu mice and SRBC ($1 \times 10^5$ cells) were mixed in 200 μl of RPMI-1640 medium and incubated for 5 days at the volume of 200 μl/well in 96-well microplate (Coster Co., USA). After 5 days splenocytes were recovered from each well, and antibody forming cells appeared by Cunningham's method were determined. As given in Table 7, induction of antibody formation was observed only in the group to which IL-2 sample was administered.

TABLE 7

Induction of antibody formation by in vivo administration of IL-2 (PFC/culture)

| IL-2 administration | Antigen (cells/well) | |
|---|---|---|
| | 0 | $1 \times 10^5$ |
| − | 4 | 2 |

TABLE 7-continued

| Induction of antibody formation by in vivo administration of IL-2 (PFC/culture) | | |
|---|---|---|
| IL-2 | Antigen (cells/well) | |
| administration | 0 | $1 \times 10^5$ |
| + | 3 | 259 |

EXAMPLE 11

Elongation of life span in tumor-(focus) removed animals

C57BL/6 were subcutaneously transplanted with syngeneic tumor, EL-4, ($3 \times 10^6$ cells/0.1 ml), and, on the 14th day wherein tumor grew enough, this solid tumor was surgically removed by nylon string and a wound was sutured by cut-band. On the next day IL-2 (100 u/0.1 ml) was i.v. administered, followed by i.v. injecting IL-2 3 times in every 4 days, and the survival numbers of mice in each group were counted. As shown in Table 8, marked elongation of life span was observed only in the group wherein purified IL-2, prepared in Table 1, was administered.

TABLE 8

| Effect of medical treatment or IL-2 administration on the EL-4 tumor removed mice | | | | |
|---|---|---|---|---|
| Transplantation of EL4 | Surgical operation | IL-2 administration | Average survival days | Survival number in 30 days after operation/number of used mice |
| $3 \times 10^6$ | — | — | 28 | — |
| $3 \times 10^6$ | + | — | 36 | 5/40 |
| $3 \times 10^6$ | — | $+^{(1)}$ | >52 | 38/40 |
| $3 \times 10^6$ | + | $+^{(2)}$ | 38 | 7/40 |

[1] purified IL-2, grade E, prepared in Table 1
[2] purified IL-2, grade C, prepared in Table 1

EXAMPLE 12

Effect of medical treatment with IL-2 on tumor metastasis after surgical removal of tumor It is considered to be the most promising target to immunotherapeutically remove a little amount of residual tumor cells after surgical operation. In this experiment, metastatic syngeneic tumors in mice, such as L1210, P388D$_1$ and MH134, were used as target.

Figure 6A:
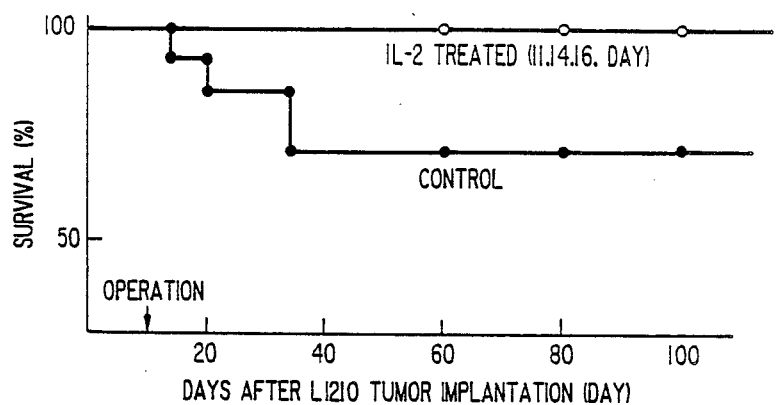

Tumor cells, L1210, ($3 \times 10^4$ cells) were subcutaneously transplanted into foot-pads of BDF$_1$ mice, and on the 10th day the transplanted portion was removed. In the experimental group wherein 100 u/0.1 ml of IL-2 was administered, all of the mice treated as above were completely cured, while in the control group without administration of IL-2 40% of mice died (FIG. 6A).

Figure 6B:
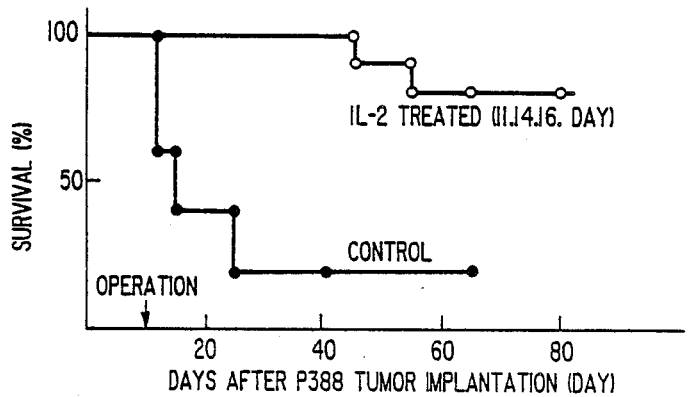

When P388D$_1$ cells ($1 \times 10^5$ cells) were administered in BDF$_1$ mice as well as the above mentioned, 80% of mice were completely cured in the IL-2-administered group, while 80% of mice died in the group without IL-2 administration. (FIG. 6B).

Figure 6C:
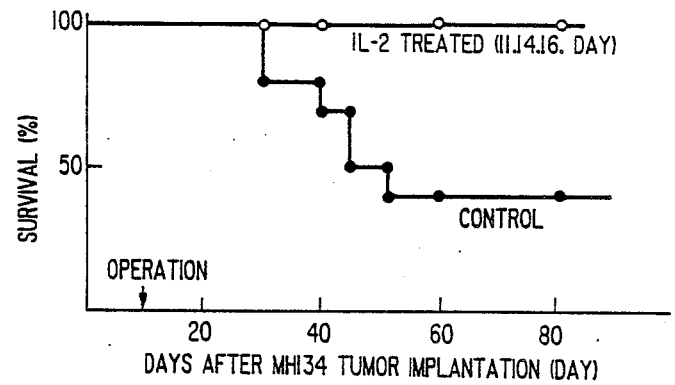

Similarly, when MH134 cells ($1 \times 10^5$ cells) were subcutaneously transplanted into food-pads of C3H/HeN mice, followed by treating with or without IL-2 as well as the above, all of the mice administered with IL-2 were completely cured. In the control group, 60% of mice died in 60 days after surgical operation. (FIG. 6C).

These experimental results were observed only when purified IL-2, grade E shown in Table 1, was administered, but not clearly observed in the experimental group with crude IL-2 preparation.

EXAMPLE 13

Elongation of life span under the combination therapy with chemotherapeutic agents in autologous tumor bearing mice 3-Methylchloranthren (MC) suspended in olive oil (0.5 mg/0.1 ml) was subcutaneously injected in the waist part of SWM/MS mice, and all the mice in which tumor grew enough to be detected as around 0.5 cm in size in diameter in 15 weeks were divided into 3 groups. 1st group were used as control and, in 2nd group, mice were i.p. administered with 100 mg/kg of cyclophosphamide (on the first day). In 3rd group, 100 u/0.1 ml of IL-2 was intravenously injected into the tail of mice on the 20th, 22nd, 24th, 26th, 28th and 30th days after administration of cyclophosphamide (100 mg/kg). Then average survival days were measured in each groups.

The average survival days were 45.0 days, 45.5 days and 123.8 days in control group, cyclophosphamide administration group (2nd group) and combination therapy group, that is Cyclophosphamide and IL-2 (3rd group), respectively. Marked elongation of life span was observed only in the combination therapy group, and IL-2 was proved to have anti-neoplastic effects against autologous tumor, too, in combination with chemotherapeutic agent.

EXAMPLE 14

Life Span elongation in syngeneic tumor bearing animals in combination with tumor antigen Mouse leukemic cells, LSTRA, were X-ray irradiated (8,000R) to remove tumorgenesity and employed as tumor vaccine, or tumor antigen. X-ray irradiated LSTRA, or its dead cells ($1 \times 10^6$ cells) was injected into food-pad of BALB/C mice. Then IL-2 (50–100 u/0.05 ml) was intravenously injected on the 5th, 7th and 9th days after vaccine injection, followed by injecting viable LSTRA cells ($1 \times 10^6$ cells) into foot-pad of these mice on the 28th day, and survival mice were observed. Survival numbers of mice in 50 days after tumor transplantation are shown in Table 9, wherein the effect of medical treatment with IL-2 in combination with tumor antigen was proved, and IL-2 was proved to have some role as adjuvant against various antigens and to be effective not only in medical treatment but also in prevention.

TABLE 9

| Life span elongation in tumor,- or LSTRA-bearing animals in combination therapy with tumor antigen | | | |
|---|---|---|---|
| Cell number of LSTRA administered as tumor antigen[1] | Cell number of LSTRA transplanted | IL-2 administered[2] (unit/head) | Survival number in 50 days/ treated number of mice |
| $10^6$ | $10^6$ | — (saline) | 4/30 |
| $10^6$ | $10^6$ | 50 | 24/30 |
| $10^6$ | $10^6$ | 100 | 28/30 |
| $10^6$ | $10^7$ | — | 0/30 |
| $10^6$ | $10^7$ | 100 | 20/30 |

[1] X-ray irradiated (8,000 R) LSTRA cells were used as antigen.
[2] IL-2 preparation employed was grade E shown in Table 1.

EXAMPLE 15

Regression of syngeneic tumor with single therapy and life span elongation of tumor bearing animals DBA/2 mice were subcutaneously transplanted in their back with $1 \times 10^6$ P815-X$_2$ mastocytoma, and IL-2 (100 u/0.1 ml) was intravenously injected 5 times on 14th, 16th, 18th, 20th and 22nd days, respectively. Both tumor regression ratio from solid tumor weight in 4 weeks and survival number of DBA/2 mice in 100 days were determined. As shown in Table 10, marked antineoplastic effects were observed in terms of tumor regression and life span elongation, and IL-2 was found to give anti-neoplastic effects even by single therapy.

TABLE 10

Anti-neoplastic effects with single therapy of IL-2

| Cell number of P815 transplanted (S.V.) | IL-2 administered (unit/head) | Tumor regression ratio in 28 days | Survival number of mice in 100 days/ treated mice |
|---|---|---|---|
| $1 \times 10^6$ | control (saline) | — | 0/40 |
| $1 \times 10^6$ | 100[1] | 89 | 33/40 |
| $1 \times 10^6$ | 100[2] | 24 | 4/40 |

[1] Grade E IL-2
[2] Grade C IL-2

EXAMPLE 16

Life span elongation against bacterial infection ddY mice were i.p. injected with E. coli No. 42 ($5 \times 10^7/0.2$ ml) grown in Difco nutrient broth, followed by intravenously injecting IL-2 (10~200 u/0.1 ml) into the tail of mice on the 3rd day before and on the 1st day after E. coli infection, and survival number of mice on the 2nd day after bacterial infection were determined as shown in Table 11A.

TABLE 11A

Anti-infectious effects against E. coli

| IL-2 administered (unit/head/day) | Survival number |
|---|---|
| Control (saline) | 0/10 |
| 10 | 1/10 |
| 15 | 3/10 |
| 100 | 10/10 |
| 200 | 10/10 |

Similarly ddY mice were i.p. injected with *Klebsiella pneumoniae* No. 19 ($5 \times 10^6/0.2$ ml), followed by administrating IL-2 (10~200 u/head) one hour after bacterial infection, and survival number of mice on the 5day after infection was determined as shown in Table 11B.

TABLE 11B

Anti-infectious effects against *K. Pneumoniae*

| IL-2 administered (unit/head/day) | Survival number |
|---|---|
| Control (saline) | 2/10 |
| 10 | 2/10 |
| 50 | 3/10 |
| 100 | 8/10 |
| 200 | 9/10 |

EXAMPLE 17

Life span elongation against viral infection (BALB/C×C57BL/6) F$_1$ mice was infected with Vesicular stomatitis virus (VSV) ($1.2 \times 10^5$ pfc unit/0.05 ml) by way of the nasal cavity under ether anaesthetic, and anti-viral activity of IL-2 was demonstrated.

IL-2 (50 u/0.05 ml each) was i.v. administered everyday from the 3rd day before to the 5th day after viral infection. In control group without IL-2 administration, 80% of mice died in 8 days, while 100% of mice still survived in 15 days in the experimental group with IL-2 administration marked anti-viral effects with IL-2 was observed in term of medical treatment effect.

EXAMPLE 18

Regressive effects against syngeneic tumor in combination with lentinan

C3H/HeN mice were s.c. transplanted with syngeneic tumor, MM102 ($3 \times 10^6/0.1$ ml), followed by administrating lentinan on the 0, 7th, and 14th days after tumor transplantation (1 mg/kg, i.v.) and, at the same time, 10 u/0.1 ml of IL-2 were i.p. injected on the 2nd day after lentinan administration. Inhibition ratio of tumor growth was determined in terms of tumor size on the 35th day after tumor transplantation, and the survival number of mice was counted 70 days after tumor transplantation. As shown in Table 12, antitumor effects of Il-2 was observed in combination therapy with lentinan.

TABLE 12

Regressive effect on the growth of syngeneic tumor in combination with lentinan

| Lentinan administration | | IL-2 administration* | | | |
|---|---|---|---|---|---|
| Amounts of administered (mg/kg) | Day after tumor transplantation | Amounts of administered (unit/head) | Day after tumor transplantation | Tumor regressive ratio (%) | Survival number/treated mice |
| control | control | control | control | 0 | 3/12 |
| 1 | 0 | — | — | −2.3 | 2/12 |
| 1 | 7 | — | — | −4.5 | 4/12 |
| 1 | 14 | — | — | 42 | 7/12 |
| 1 | 14 | 10 | 16 | 78 | 12/12 |

*grade E IL-2

What is claimed is:

1. An immunoprophylactic and immunotherapeutic agent, composition comprising grade E human interleukin 2 of human T-lymphocyte cell origin, which is substantially free from endotoxins and pyrogens and is wholly or partially in the oxidized state, having a specific activity of at least $2 \times 10^5$ units/mg protein, said interleukin 2 showing no cytocidal activity against human lymphocytes in vitro at a concentration of $10^5$ units/ml and having substantially no other lymphokine or monokine activity, in combination with an amount of lentinan sufficient to exert synergistic immunological activity.

* * * * *